(12) United States Patent
Simon

(10) Patent No.: US 7,052,456 B2
(45) Date of Patent: May 30, 2006

(54) AIRWAY PRODUCTS HAVING LEDS

(76) Inventor: James S. Simon, P.O. Box 726, Tiburon, CA (US) 94920

( * ) Notice: Subject to any disclaimer, the term of this patent is extended or adjusted under 35 U.S.C. 154(b) by 0 days.

(21) Appl. No.: 10/417,749

(22) Filed: Apr. 16, 2003

(65) Prior Publication Data
US 2004/0210114 A1 Oct. 21, 2004

(51) Int. Cl.
*A61B 1/00* (2006.01)
(52) U.S. Cl. .................. 600/120; 600/185; 600/194; 600/207; 600/245
(58) Field of Classification Search ............ 600/120, 600/185, 194, 207, 245
See application file for complete search history.

(56) References Cited

U.S. PATENT DOCUMENTS

| | | |
|---|---|---|
| 3,350,553 A | 10/1967 | Cline |
| 3,539,794 A | 11/1970 | Rauhut et al. |
| 3,576,987 A | 5/1971 | Voight et al. |
| 3,716,047 A | 2/1973 | Moore et al. |
| 3,729,425 A | 4/1973 | Andress et al. |
| 3,808,414 A | 4/1974 | Roberts |
| 3,893,938 A | 7/1975 | Rauhut |
| 4,150,676 A | 4/1979 | Jackson |
| 4,635,166 A | 1/1987 | Cameron |
| 4,814,949 A | 3/1989 | Elliott |
| 5,005,573 A * | 4/1991 | Buchanan ............ 128/207.14 |
| 5,179,938 A | 1/1993 | Lonky |
| 5,241,956 A | 9/1993 | Brain |
| 5,249,571 A | 10/1993 | Brain |
| 5,282,464 A | 2/1994 | Brain |
| 5,285,778 A * | 2/1994 | Mackin ............... 128/207.15 |
| 5,287,848 A | 2/1994 | Cubb et al. |
| 5,297,547 A | 3/1994 | Brain |
| 5,305,743 A | 4/1994 | Brain |
| 5,329,938 A | 7/1994 | Lonky |
| 5,329,940 A | 7/1994 | Adair |
| 5,348,690 A | 9/1994 | Cohen et al. |

(Continued)

FOREIGN PATENT DOCUMENTS

WO    WO 02/056951    7/2002

(Continued)

OTHER PUBLICATIONS

Adair (2001). Macintosh Lighted Stylet, located at <http://www/adair.at/eng/museum/equip/acctracheal/macintoshlighted.html> last visited on Mar. 28, 2003.

(Continued)

*Primary Examiner*—Beverly M. Flanagan
(74) *Attorney, Agent, or Firm*—Thomas M. Freiburger

(57) ABSTRACT

The present invention relates to an illuminated airway product that will allow visualization of the airway of a patient during intubation. The illuminated airway product includes a light source such as an LED disposed at its distal end. The LED shines axially, radially, or in both directions from the airway intubation device. The airway product includes an on-board voltage source. Hence, no additional or external voltage sources or components are necessary to light the device. The airway device may further include one or more lumens or tubes for delivering air, suctioning debris or fluids, delivering medicine, radio-opaqueness, etc. An inflatable cuff may be associated with the endotracheal tube such that collateral flow of air is prevented. An inflation lumen or tube is fluidly coupled to the inflatable cuff. The shape of the endotracheal tube may be adjusted either by use of a stylet or suction trocar made out of a malleable material such as aluminum or by inclusion of a malleable wire within the tube. Kits including a LED lighted endotracheal tube are also provided.

15 Claims, 9 Drawing Sheets

U.S. PATENT DOCUMENTS

| | | | |
|---|---|---|---|
| 5,355,879 | A | 10/1994 | Brain |
| 5,400,771 | A | 3/1995 | Pirak et al. |
| 5,457,613 | A | 10/1995 | Vandenbelt et al. |
| 5,488,544 | A | 1/1996 | Ladyjensky |
| 5,552,968 | A | 9/1996 | Ladyjensky |
| 5,569,300 | A | 10/1996 | Redmon |
| 5,607,386 | A | 3/1997 | Flam |
| 5,665,052 | A * | 9/1997 | Bullard ..................... 600/194 |
| 5,676,635 | A * | 10/1997 | Levin ........................ 600/120 |
| 5,716,329 | A | 2/1998 | Dieter |
| 5,775,322 | A | 7/1998 | Silverstein et al. |
| 5,819,727 | A | 10/1998 | Linder |
| 5,941,816 | A | 8/1999 | Barthel et al. |
| 6,004,265 | A | 12/1999 | Hsu et al. |
| 6,024,697 | A | 2/2000 | Pisarik |
| 6,050,713 | A | 4/2000 | O'Donnell et al. |
| 6,067,985 | A * | 5/2000 | Islava .................... 128/207.17 |
| 6,142,935 | A | 11/2000 | Flom et al. |
| 6,161,537 | A | 12/2000 | Gravenstein et al. |
| 6,176,824 | B1 | 1/2001 | Davis |
| 6,189,533 | B1 * | 2/2001 | Simon et al. .......... 128/207.14 |
| 6,228,025 | B1 | 5/2001 | Hipps et al. |
| 2002/0162557 | A1 | 11/2002 | Simon et al. |
| 2005/0065496 | A1 | 3/2005 | Simon et al. |

FOREIGN PATENT DOCUMENTS

| | | |
|---|---|---|
| WO | WO-03/075979 A2 | 9/2003 |
| WO | WO-04/093791 A2 | 11/2004 |

OTHER PUBLICATIONS

Anonymous (2002). "Intubation-Advances Airway Management (#10102.)" Procedure 2 pages.

Anonymous (2003). "Anatomic Landmarks," located at <http://www.rnceus.com/resp/respthoracic.html> last visited on Apr. 2, 2002. 2 pages.

Birmingham et al. (1986). "Esophageal Intubation: A Review of Detection Techniques," *Anesth. Analg.* 65:886-891.

Debo, R.F. et al. (1989). "Cricoarytenoid Subluxation: Complication of Blind Intubation With a Lighted Stylet," *Ear, Nose, Throat Journal* vol. 68, 3 pages.

Dey, D. et al. (No Date Available). "Mixed Reality of Merging of Endoscopic Images and 3-D Surfaces," 8 pages.

Graphic Solutions, Inc. (2003). Thin Flexible Battery product information sheets located at <http://www.graphicsolutionsinc.com/tfb.html> last visited on Mar. 26, 2003. 3 pages.

Heller, R.M. and Heller, T.W. (1994). "Experience With the Illuminated Endotracheal Tube in the Prevention of Unsafe Intubations in the Premature and Full-Term Newborn," *Pediatrics* 93(3):389-391.

Hendrickson, G. (2001). "Intubation" located at <http://atoz/iqhealth.com/HealthAnswers/encyclopedia/HTMLfiles/1219.html> last visited on Apr. 2, 2003. 2 pages.

Hudson RCI Brochure (No Date Available). Airway Management product sheets, pp. 1-22.

King, H.-K. (2002). "Soft-tip Intubating Stylet," *Brief Communication: Acta Anaethesiol Sin* 40:135-137.

Lumex, Inc. (1997-2001). T-1.88mm Stove Pipe Lens LED Lamp product sheet, located at <http://www.lumex.com/pls/lumex/subproduct_galary> last visited on Mar. 31, 2003, 1 page.

Lumex, Inc. (1997-2001). T-2mm Axial Leaded LED Lamp product sheet, located at <http://www.lumex.com/pls/lumex/subproduct_galary> last visited on Mar. 31, 2003, 2 pages.

Luxeon Dental Brochure (2002). "Power Light source," Luxeon Dental Technical Data DS35, 10 pages.

Mercury Medical Catalog (No Date Available). Intubation Products, 24 pages.

Nellcor Product Brochure (2003). Hi-Lo Tracheal Tube product sheet located at <http://www.nellcor.com/prod/Product.aspx?> last visited on Mar. 27, 2003. 1 page.

Nellcor Puritan Bennett Inc. (2003). Disposable Cannula Cuffed Tracheostomy Tubes product information sheet located at <http://www.nellcor.com/prod/Product.aspx?> last visited on Mar. 27, 2003.

Nellcor Puritan Bennett Inc. (2003). Disposable Cannula Cuffless Tracheostomy Tubes Product Information sheet located at <http://www.nellcor.com.prod/Product.aspx?> last visited on Mar. 27, 2003. 1 page.

Nellcor Puritan Bennett Inc. (2003). EMT Emergency Medicine Tube Product Fact Sheet located at <http://www.nellcor.com/prod/Product.aspx> last visited on Mar. 27, 2003, 1 page.

Nellcor Puritan Bennett Inc. (2003). Laser-Flex Tracheal Tube Product Fact Sheet located at <http://www.nellcor.com/prod/Product.aspx> last visited on Mar. 27, 2003, 1 page.

Power Paper Ltd. Brochure (2003). Power Paper, Micro-Powered Devices, Thin and Flexible Batteries located at <http://www.powerpaper.com/3_technology/advantage.html> last visited on Mar. 27, 2003. 6 pages.

Quallion, LLC Product Sheet (2002). I Series Product Feature Fact Sheet, located at <http://www.quallion.com/prod_i.html> last visited on Apr. 2, 2002. 1 page.

Seiko Instruments, Inc. (2002) Micro Batteries Product Catalogue. 28 pages.

Tech:Med Brochure: Face Shields and Product Masks, pp. 21-28.

International Search Report mailed on Apr. 7, 2005 for PCT Patent Application No. PCT/US04.11773 filed on Apr. 16, 2004, 2 pages.

* cited by examiner

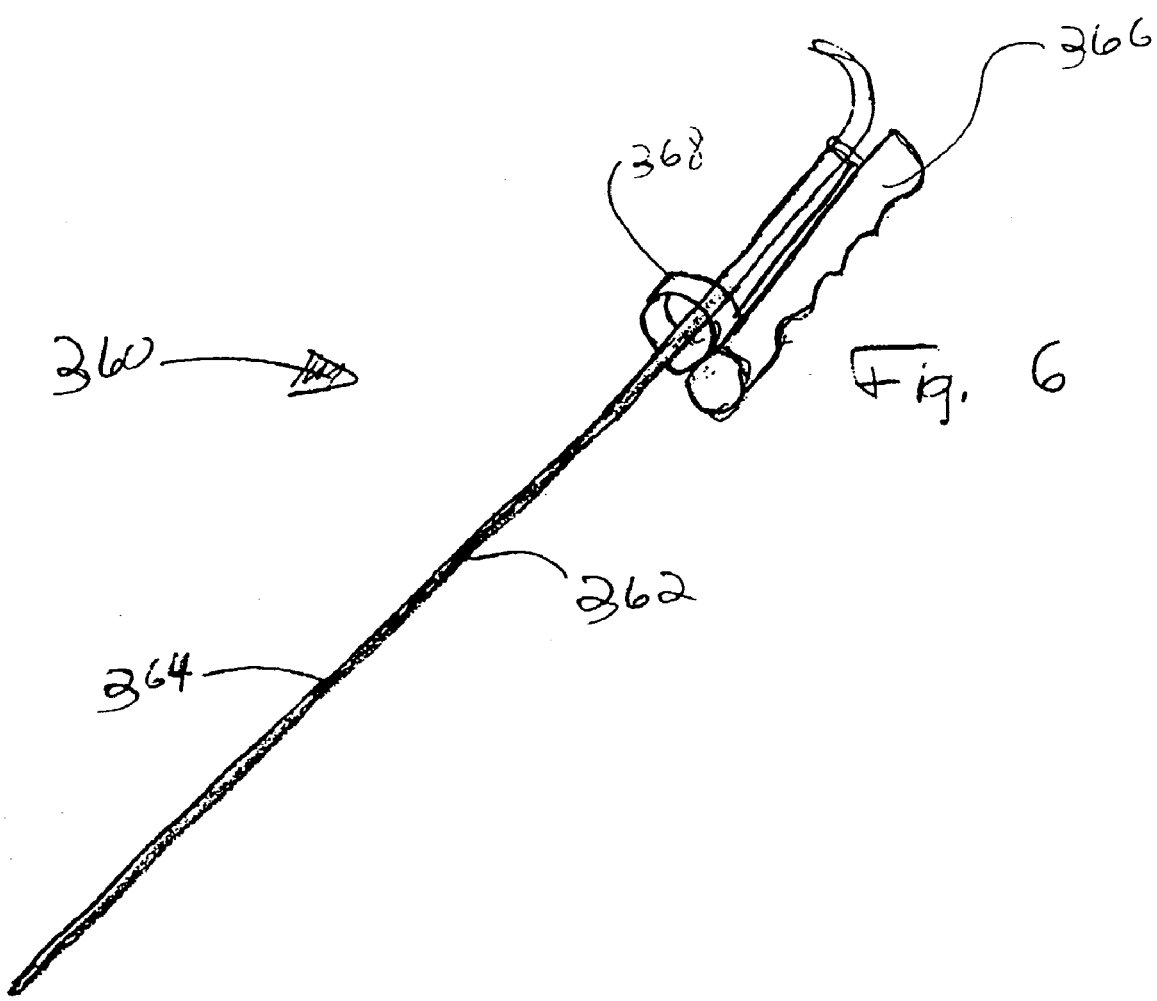

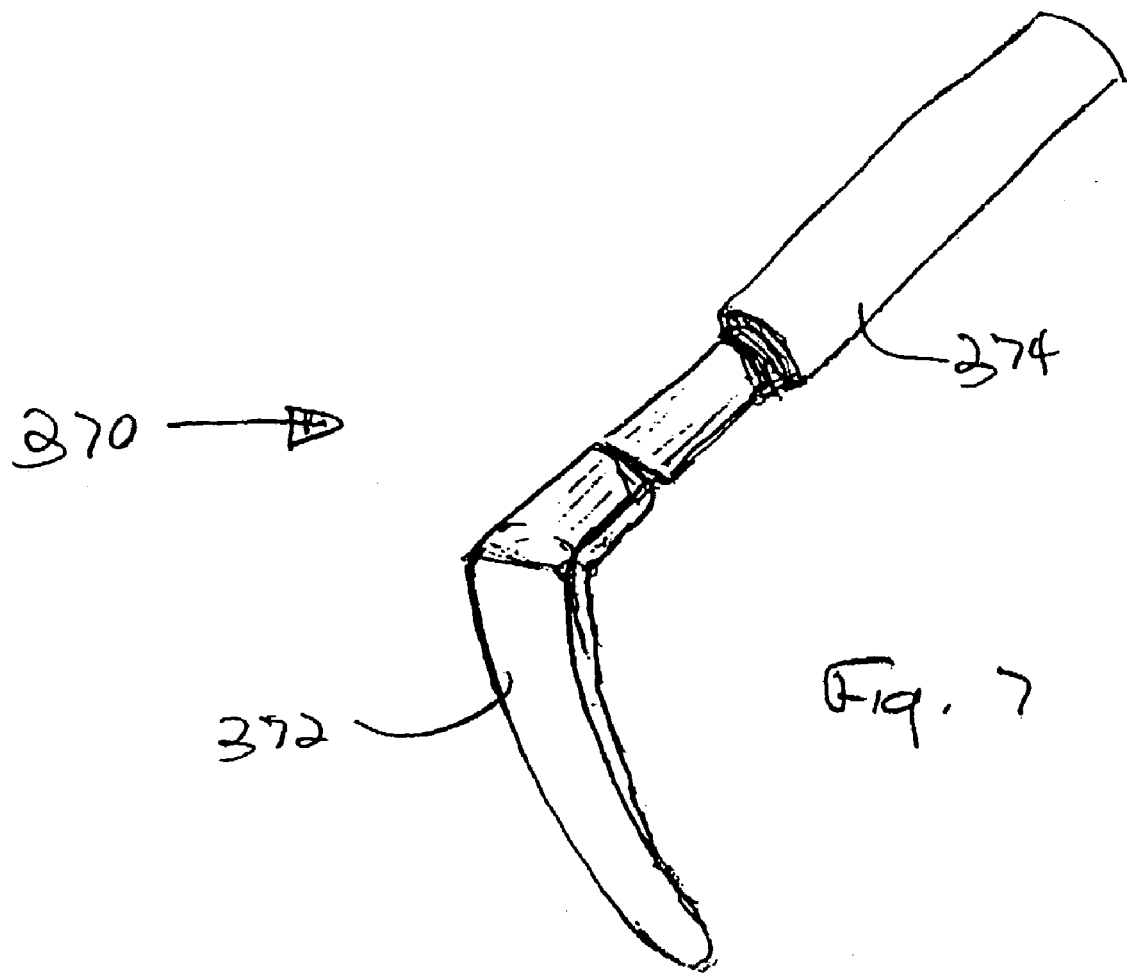

AIRWAY PRODUCTS HAVING LEDS

BACKGROUND OF THE INVENTION

This invention generally relates to medical devices and more particularly to an airway product having a light source in its distal end for illumination during intubation.

DESCRIPTION OF RELATED ART

Endotracheal intubation is a medical procedure that is used to establish a secure direct path for air under emergency resuscitation conditions or during induction of general anesthesia. In a typical intubation procedure, an intubator or medic manipulates an endotracheal tube (ETT) through the vocal cords and into the trachea. A breathing bag may be connected to the proximal end of the ETT to supply air through the ETT into the patient's lungs.

A number of problems, however, are faced in performing an intubation. For example, the natural airway can become obstructed, either by a foreign body or by fluid, blood, or tissues such as the patient's tongue. Additionally, a patient in a major arrest state is unable to move air and as a result death rapidly ensues in the absence of introduced oxygen through the airway. Additionally, lighting is often inadequate and foreign bodies, fluids, blood, loose dentures, or a flaccid tongue may compromise visualization of the vocal cords.

Positioning the end of the ETT in the proper location along the trachea is also crucial in an intubation. In particular, the inserted end of the endotracheal tube should be positioned in the patient's trachea at a location substantially between the patient's vocal cords and carina. This location has been found to provide the best and most reliable airway management for several reasons. If the tube is not inserted far enough past the vocal cords, for example, it can become dislodged and ineffective, such as when it ends up in the esophagus. If the tube is inserted too far into the trachea, however, past the carina, then the tube may only function to adequately ventilate one of the lungs, rather than both. This can lead to serious complications. Thus, proper placement of the inserted end of the tube plays a major role in the intubation process.

One intubation technique that attempts to overcome some of the above mentioned problems is direct laryngoscopy. During a laryngoscopy intubation procedure, a practitioner holds a lighted laryngoscopic blade in one hand, to elevate the palate and improve visualization, and a suction tube in the other hand, to remove loose debris that may be blocking visualization. An ETT is then inserted into the trachea. However, a drawback of this lighted-laryngoscope technique is that in order to introduce the endotracheal tube, the suction must be put aside, thereby compromising visualization.

Another technique is the fiber-optic bronchoscopic technique. The fiber-optic bronchoscopic technique allows visualization of the vocal chords and trachea to confirm correct ETT placement. However, major drawbacks of the fiberscopic technique are (1) that it requires substantial expertise and (2) its poor performance in patients with copious secretions or blood in their airway. Thus, the patient is usually administered an anti-sialagogue to decrease secretions and a topical vasoconstrictor to reduce bleeding caused from the trauma that can be associated with oral and nasal intubations. Because blood so easily compromises the fiberscopic view and renders the fiberscope useless, it is often impractical and unnecessarily time-consuming to attempt this method of intubation in the traumatized victim. Although advances have been made in miniaturization of the fiberscope, the smaller-diameter fiberscopes that will pass through the smallest diameter ETTs are prohibitively expensive. Further drawbacks to the fiberscope are that it requires an external power supply for its light source, it is a large instrument and occupies substantial space at the patient's head, as well as for storage. Also, fiberscopes tend to be expensive and sensitive instruments that are easily broken.

Another intubation technique involves a retrograde guidewire. This method requires that a needle be placed through the anterior neck into the trachea. A wire is passed through the needle and is then advanced upward through the vocal cords and pharynx until it emerges from the nose or mouth. The wire acts as a guide for either an ETT alone or a fiberscope loaded with an ETT. This method identifies the most prominent anatomical structure in the neck, namely, the trachea, and establishes a path for the ETT or fiberscope to follow in order to properly place the ETT there. One drawback to this technique is that it is invasive and risks introducing bleeding and infection into the trachea. Another drawback is that the wire must be stiff enough to act as a guide for the ETT alone. A stiff wire is more prone to injure tissues such as the trachea and vocal cords when advanced than would a more flexible wire. If the wire can act only as a visual guide for the fiberscope, then this method is also disadvantaged in bloody or secretion-abundant environments.

The lighted stylet is a device that incorporates aspects of both the fiberscope and retrograde wire techniques. In design, it is simply a stylet with a light bulb at the distal end and a battery power source at the other end. An ETT is loaded over the stylet such that the light just emerges from the distal end of the ETT. When properly placed in the mouth, the light from the stylet will shine between the vocal cords into the trachea and the operator will see a pre-tracheal glow on the external neck. Once this glow is identified, the ETT is advanced and proper ETT placement reconfirmed through customary means. See Birmingham et al, Anesth. Analg., Vol. 65, pp. 886–891 (1986). Thus, the lighted stylet is like the fiberscope in that it uses a light source in the airway and that the stylet acts as a platform from which to place the ETT. It is like the retrograde wire in that it guides the ETT into position.

The lighted stylet overcomes many of the disadvantages of the fiberscope and retrograde wire techniques. Unlike the fiberscope, the lighted stylet is small, easily stored, rugged, does not require an extra power source, is disposable, relatively inexpensive and works well in a bloody environment. Unlike the retrograde wire technique, it does not risk additional infection or bleeding, and acts as its own ETT placement platform. However, intubating with a stylet is typically not as rapid as intubating with a laryngoscope. Additionally, a report indicates cricoarytenoid subluxation after blind intubation with a light wand. See Debo et al., Cricoarytenoid Subluxation: Complication Of Blind Intubation With A Lighted Stylet, Ear Nose Throat J. 68:517–520 (1989).

Another technique involves a lighted intubation tube. See Heller et al., Experience With The Illuminated Endotracheal Tube In The Prevention Of Unsafe Intubations In The Premature And Full-Term Newborn, Pediatrics, v93, no. 3, p389–391 (1994). In the Heller reference a fiber optic strand is incorporated into the wall of the endotracheal tube. Prior to intubation, the endotracheal tube is connected to a light source. A drawback of the device described in Heller is that the ETT is not self-illuminating. It requires an external light source and connection hardware. Also, an external voltage supply is required.

The present invention is designed to overcome the aforementioned difficulties during intubation. The invention includes a self-illuminating endotracheal tube with a bright light (and voltage) source built-in. The light source is a LED associated with the distal end of the endotracheal tube. The LED may shine either axially or radially from the distal end of the endotracheal tube. The lighted endotracheal tube may include a connection to a suction source and a malleable wire for adjustment of the shape of the tube under emergency conditions such as cardiopulmonary resuscitation.

BRIEF SUMMARY OF THE INVENTION

The invention is an illuminated airway product comprising an endotracheal tube having a proximal end, a distal end and at least one lumen extending from the proximal end to the distal end. A LED is mounted at the distal end of the endotracheal tube. A voltage source is electrically coupled to the LED. The voltage source is secured to the endotracheal tube. Hence, external voltage sources or light sources are not required.

The LED may shine various colors including, for example, white, red, blue, yellow, orange, etc. The light may be directed axially or radially, or both. A LED may be configured or positioned such that light is directed distally or proximally from the end of the ETT. Lens elements may be optically coupled to the LED to direct light.

A switch may be secured to the endotracheal tube that can activate the LED. The switch may include two conductive strips. The intubator may join the two conductive strips together. She may simply touch one strip against the other to complete an LED circuit.

The switch may be resiliently biased in an OFF state and the intubator presses a button to activate the switch. When the button is released, the circuit is open and the LED is not activated. Also, the switch may be unbiased such that the operator must manually turn on and off the switch.

The voltage source is generally a small battery having a disc or cylindrical shape. Thin flexible batteries may also be associated with the device to provide current to the LED. A battery assembly or shell may contain the battery and be affixed to the endotracheal tube. The switch may be mounted on (or within) the assembly such that an intubator or medic may conveniently open or close the circuit. The battery assembly may be positioned near or adjacent the proximal end of the endotracheal tube. The battery assembly should not interfere with a connector for connecting the endotracheal tube with an air or oxygen supply apparatus.

The airway product may also include a number of additional lumens or tubes. Each lumen or tube may be configured or utilized to serve a specific purpose. In one variation, the airway product includes an inflation lumen fluidly coupled to an inflatable cuff. Another variation of the invention includes a suction lumen. A suction source may be fluidly coupled to the suction lumen.

In another variation of the present invention, one of the lumens or tubes is a medicinal supply lumen. In yet another variation, one of the lumens or tubes is filled with a radio-opaque member that allows the airway product to be visualized.

The airway product may additionally include a malleable stylet. The stylet may be malleable such that the intubator may adjust the curvature of the endotracheal tube and it will hold its shape. Also, the stylet tip may be inserted to a target area and the endotracheal tube may be delivered into the position over the stylet.

A kit for performing an intubation procedure comprises an endotracheal tube having a proximal end, a distal end and at least one lumen extending from the proximal end to the distal end. The ETT also includes a LED mounted at the distal end of the endotracheal tube. The LED is electrically coupled to a voltage supply which is secured to the endotracheal tube. The kit additional includes a laryngoscope having a curved blade adapted to manipulate tissue and assist in guiding the endotracheal tube into position.

The kit may include one or more additional components including a suction catheter, a fiberoptic scope, a medicinal delivery catheter, a stylet, a radio-opaque member, an ETT holder, or another tool.

The kit may further include an oxygen supply apparatus fluidly coupled to the lumen of said endotracheal tube. The oxygen supply apparatus may be a breathing bag, respirator or another device that can provide air or oxygen.

BRIEF DESCRIPTION OF THE DRAWINGS

FIG. 6 shows an illuminated stylet as may be used during intubation.

FIG. 7 shows an illuminated laryngeal blade that may also be used during intubation.

DETAILED DESCRIPTION OF THE INVENTION

Described herein are illuminating airway products that may be used to carry out intubation procedures. LEDs, fiber optics, and chemiluminescence materials are examples of components that may be associated with the airway products to light the anatomical structures during an intubation procedure. The lighted devices serve to illuminate the throat, larynx, epiglottis, vocal cords, and trachea during an intubation procedure. In one variation, a LED is positioned on the end of the device to direct light axially and/or radially from the endotracheal device at tissue to be visualized.

The lighted devices may also ensure that the airway product is properly located between the patient's vocal cords and the carina after intubation. LEDs mounted at the distal end of an endotracheal tube can transmit light through the cartilage and soft tissues of the neck. When the light is clearly visible through the patient's skin in the area of the sternal notch, then the inserted end of the tube may be approximately half-way between the vocal cords and carina in many patients. The absence of a clear glow of illumination in this area usually indicates incorrect placement, such as in the esophagus.

Figure 1A:
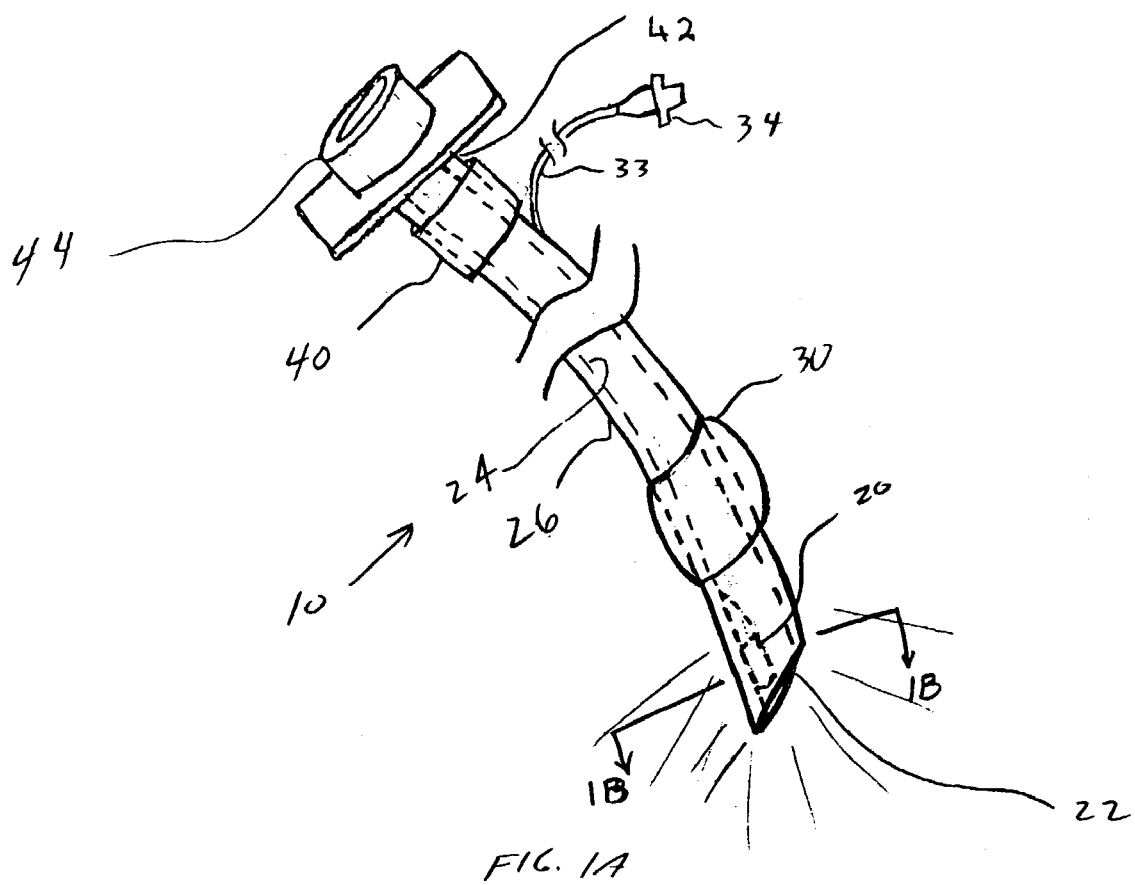
FIG. 1A is a partial perspective view of a self illuminating endotracheal tube having a LED associated with the distal end.

FIG. 1A shows an endotracheal intubation device 10 having a LED 20 at its distal end 22. The LED 20 lights both radially and axially. This is an advantage over non lighted intubation devices because the light is helpful to visualize the procedure. Additionally, the LED may be bright and shine through the skin when the device is inserted into the trachea. Consequently, the doctor or intubator may see the position of the distal tip of the endotracheal tube as it is being manipulated into proper position. If the tip is inserted too far it may enter only one lung, dramatically reducing the amount of air exchange in the patient. If the tip is inserted too shallow, the tube may be ejected or clogged. It is therefore advantageous to quickly and conveniently identify the position of the tip of the endotracheal intubation device so that the patient may be properly treated or resuscitated. It may also be desirable to dim the background lights to assist in this procedure.

Figure 1B:
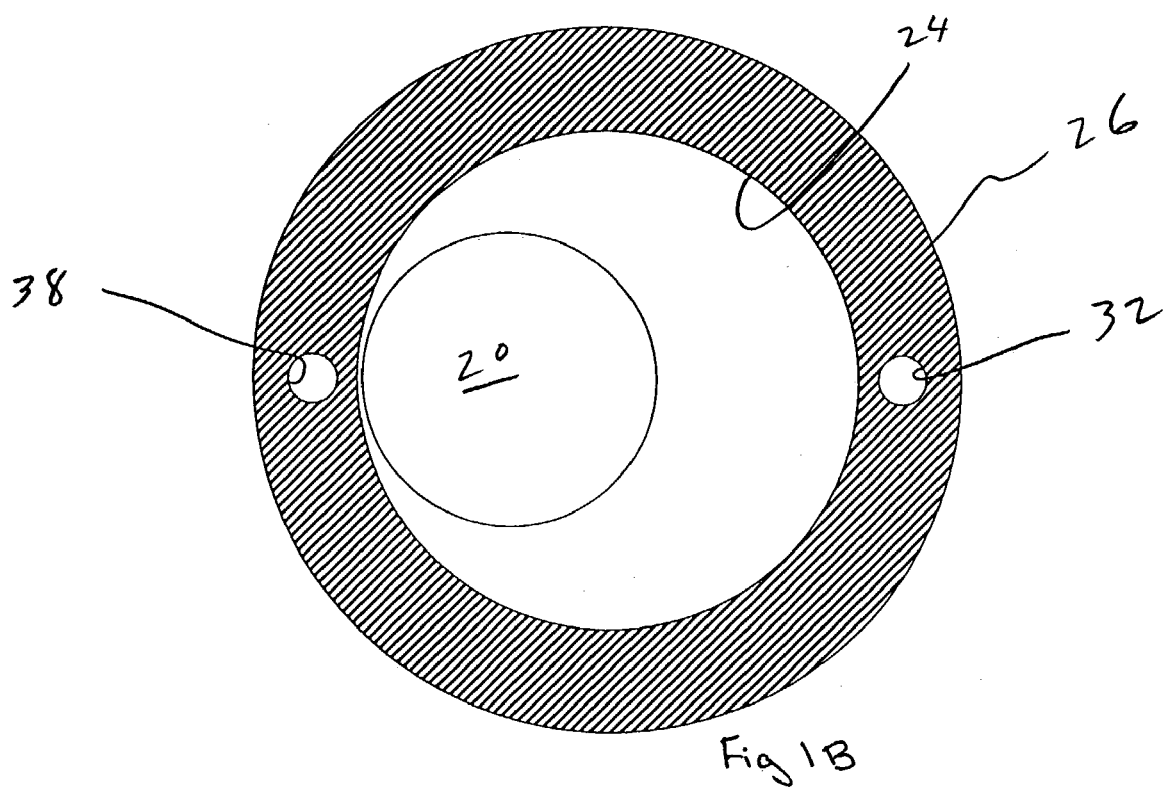
FIG. 1B is a cross sectional view of the endotracheal tube shown in FIG. 1A taken along line 1B—1B.
Figure 1C:
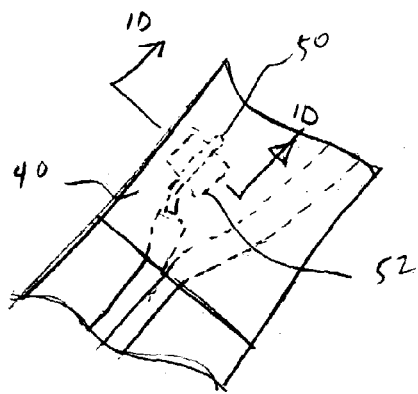
FIG. 1C is an illustration of an electrical switch, connecting a wire lead and a battery electrode of the endotracheal tube.
Figure 1E:
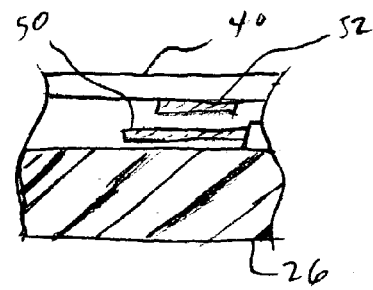
FIG. 1E is a partial sectional view of the electrical switch shown in FIG. 1D, taken along line 1E—1E.
Figure 1D:
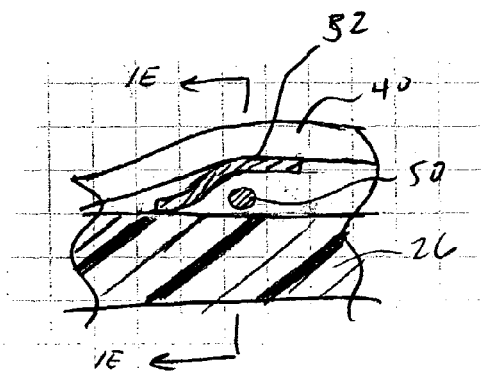
FIG. 1D is a partial cross sectional view of the electrical switch shown in FIG. 1C taken along line 1D—1D.

The LED may be mounted within a lumen 24 of the endotracheal tube 26. As shown in FIG. 1B, for example, the LED 20 is positioned against the wall of the endotracheal tube 26. The LED may be, for example, glued, taped, or otherwise bonded to the wall. The LED may be flush with the distal end of the ETT or it may be recessed such that the LED does not contact the tissue. The LED may also be positioned on the outside or extend beyond the tip of the endotracheal tube. The ETT thus may be fiber-optic free.

Examples of LEDs include T-2 mm Axial Leaded LED Lamps and T-1.8 Stove Pipe Lens Lamps both manufactured by Lumex, Inc. Palatine, Ill. However, many different types of LEDs may be associated with the distal end of the ETT to provide the light in accordance with the present invention. Additionally, lens elements (e.g., mirror, glass, or polymer elements) may be attached at the tip of the LED (or the ETT) to redirect light emitted from the LED. The light may emanate from the ETT as a cone, ring, beam, sphere, or another geometrical shape. Blinking LEDs may also be used. The color of the light emitted from the LED may be white, red, blue, orange, yellow etc. The LED may also be set in the ETT at an angle to shine light radially from the trachea. Or, the LED is positioned such that it shines light radially and axially. The light may also shine in the longitudinal direction distally and/or proximally.

The LED is electrically connected to a voltage source 40. The voltage source 40 is preferably incorporated or associated with the ETT such that the ETT is self-illuminating. An external voltage source is thus not necessary to provide illumination. Additionally, the intubator will not need to connect any cables, tubes or wires to perform a lighted intubation procedure.

The voltage source 40 may be a battery such as a micro battery having a size similar to that of a grain of rice (see, e.g., I-series, Model QL00031 manufactured by Quallion LLC, Sylmar, Calif., having a diameter of 2.9 mm and a thickness of 13.0 mm). It may also be disk shaped (see, e.g., Model No SR416SW manufactured by Seiko Instruments Inc., having a nominal voltage of 1.55 and a diameter of 4.8 mm.). Another battery type is a flat battery such as that manufactured by Polaroid. Standard-type batteries having conventional sizes may also be incorporated into the battery assembly. Another battery is a thin flexible battery (see, e.g., Model STD-1 by Power Paper, Israel having a thickness of 0.6 mm and a bending radius of 25 mm.). The battery may be a lithium battery known for long shelf life. Such voltage sources may be incorporated into the ETT near the proximal end 42 of the ETT but the voltage source should not interfere with the air connector 44.

The voltage source shown in FIG. 1A is a thin flexible battery that is wrapped around the proximal end of the ETT. It includes two electrodes that are electrically coupled to the LED. A switch, described below, activates the LED.

Figure 1F:
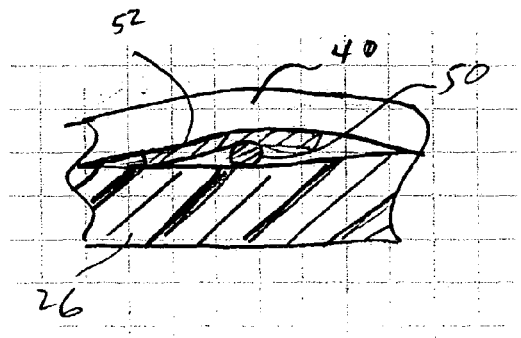
FIG. 1F is a partial cross sectional view similar to that shown in FIG. 1D except that the switch shown in FIG. 1F is in an ON state.
Figure 1G:
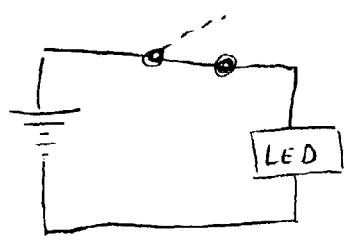
FIG. 1G is a circuit diagram of a self illuminating endotracheal tube.

An enlarged partial view of a switch is illustrated in FIGS. 1C–1F. In particular, a wire lead 50 is positioned between the wall of the ETT 26 and a displaceable electrode 52 of the battery 40 (e.g., the cathode). The displaceable electrode may be a resilient material that has an assumed first position, separating the electrode 52 from the wire lead 50. When the intubator desires to activate the LED, the displaceable electrode is depressed urging the electrode against the wire lead as shown in FIG. 1F. The circuit is closed and the LED is activated. An example of a circuit is shown in FIG. 1G.

The displaceable material may be provided such that it automatically returns to its first position, deactivating the LED when the intubator or medic releases the ETT. Examples of materials that may be used for the leads include steel, shape memory alloys, or another electrically conducting material. Alternatively, the displaceable electrode may be made of a plastically deformable material.

A biocompatible wrap or coating may coaxially surround the battery assembly. The battery assembly may include redundant layers to ensure that no materials leak. Still other battery assemblies are described further below in connection with FIGS. 1I–1H.

The overall dimensions and shape of the ETT may be similar to various conventional ETTs such as, for example, the Hi-Lo® Tracheal Tube manufactured by Nellcor Puritan Bennett, Inc. A typical inner diameter of the main lumen is 7.5 mm and upwards. However, ETTs may be much smaller in diameter. Indeed, the dimensions of the ETT may vary greatly depending on the application and patient. For example, it may be desirable to have an ETT with an OD of less than 5 mm when intubating an infant.

The ETT may also include a number of other features and lumens. The ETT shown in FIGS. 1A, 1B includes an inflatable cuff 30, inflation lumen 32, and inflation connector 34 that is adapted to connect with, for example, a syringe. Flexible tubing 33 fluidly couples the inflation lumen 32 to the inflation connector 34. Also, inflation lumen 32 is sealed (or plugged) distal to the cuff so that the cuff may be inflated when air or another fluid is delivered into the cuff member 30. Although an inflatable cuff is desirable to prevent collateral flow, it is not a necessary component for the invention. Indeed, various ETTs do not include inflatable cuffs.

The ETT may also be provided with a stylet. The stylet is manipulated into the target region of the trachea and the ETT is passed over the stylet into position. Also, a suction catheter or tube may be inserted through the lumen 24 to remove debris and mucous and other materials from the surgical regions.

As shown in FIG. 1B, the ETT may comprise one or more additional or ancillary lumens 38. Lumen 38 may serve various purposes. For example, it may be filled with a radio-opaque or vision-enhancing material to help visualize the ETT in the trachea. This lumen may be provided with a malleable wire to shape the ETT as it is inserted into position. In some variations, the ancillary lumen is fluidly coupled to a medicinal substance so that medicine may be delivered to the target site. Still other devices may be inserted through one or more of the lumens to facilitate the intubation or procedure. The ancillary lumen may also be used for holding electronic wiring to electrically couple the LED with a voltage source.

Figure 1H:
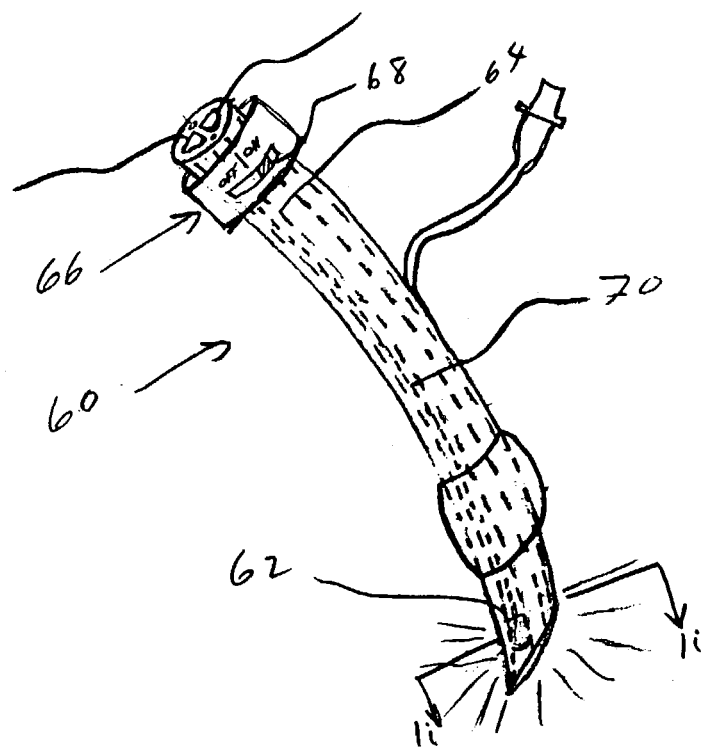
FIG. 1H is a partial perspective view of another self illuminating endotracheal tube having a LED associated with its distal end, the endotracheal tube shown in this figure includes four independent lumens.
Figure 1I:
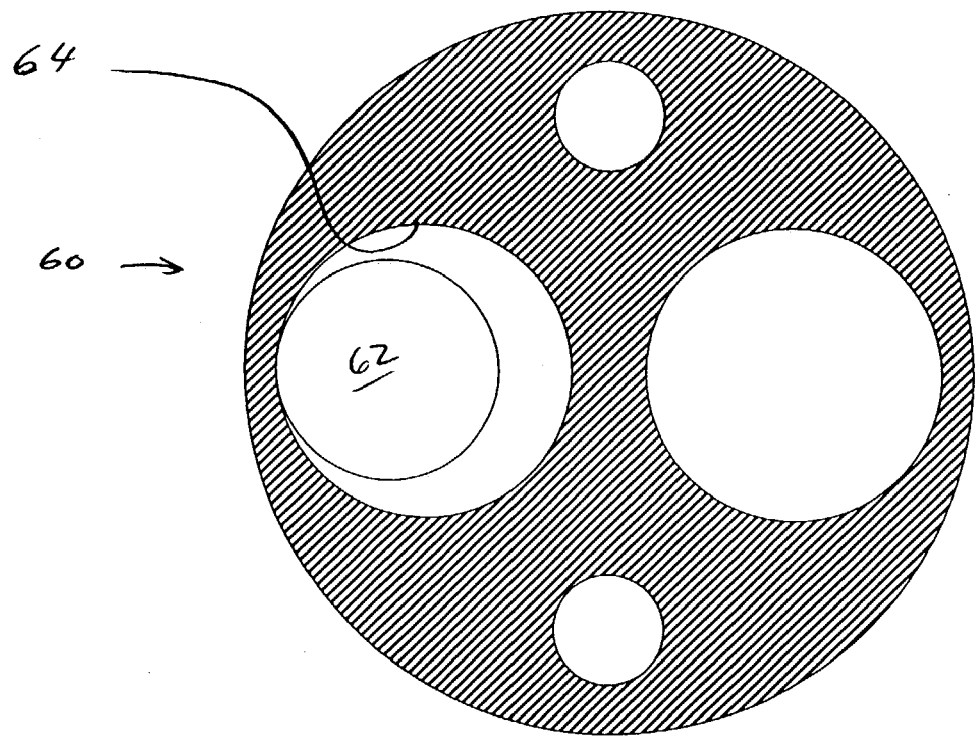
FIG. 1I is a cross sectional view of the endotracheal tube shown in FIG. 1H taken along line 1I—1I.

FIG. 1H depicts another LED illuminated endotracheal tube 60 having a LED 62 positioned at the distal end. As shown in FIG. 1I, the LED 62 is contained in a large lumen 64 of the ETT. However, unlike the ETT shown in FIGS. 1A–1B, the ETT 60 of FIGS. 1H–1I includes two large lumens and two small lumens, each of which is independent from one another. As indicated above, more or less lumens may be provided to accommodate various tools and light sources.

The ETT shown in FIG. 1H also shows a switch assembly 66. A battery (not shown) sits within the switch assembly. To activate the LED, a switch 68 is moved laterally. An insulated wire 70 electrically connects the battery to the LED. The wire extends through lumen 64 to the LED. The wire and LED may be bonded to the ETT. Also, the lumen may be filled with an epoxy to prevent air or other materials from flowing therethrough.

Other features and tools may be used with the ETT shown in FIGS. 1H–1I as discussed above in connection with FIGS. 1A–1G.

Another airway product includes an ETT and a LED positioned at the proximal end of the ETT. One or more fiber optics are electrically coupled to the LED. The fiber optic may extend to the distal end of the ETT or to another location along the ETT. Light from the LED is directed by the fiber optic and emitted radially and/or axially. The fiber optic may be secured or imbedded in the wall of the ETT. Additionally, a voltage source is electrically coupled to the LED and secured to the ETT. An electrical switch may be provided to control activation of the LED.

Figure 2:
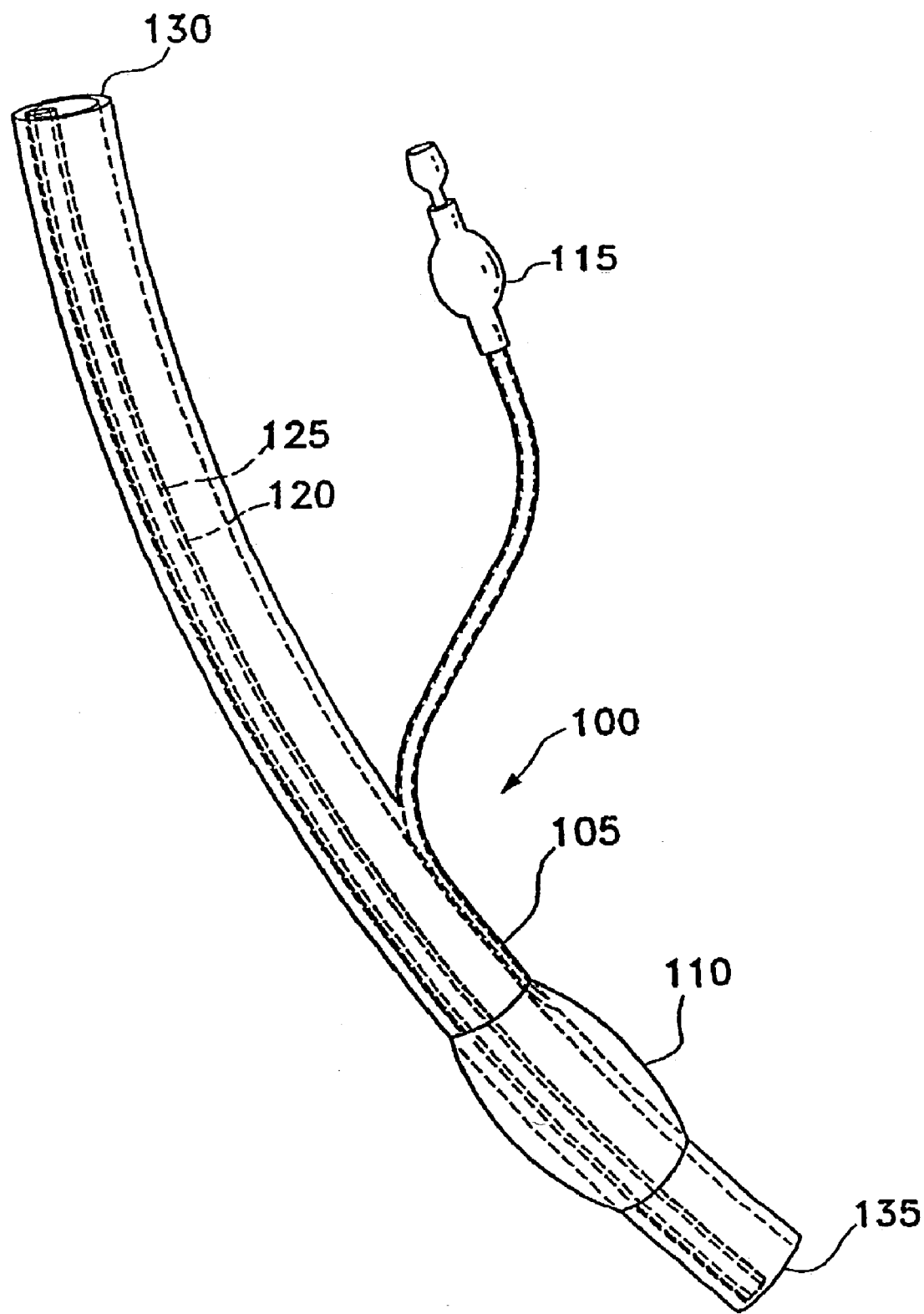
FIG. 2 is a perspective view of an endotracheal intubation device having a suction trocar and a lighted sleeve for the suction trocar.

Shown in FIG. 2 is another endotracheal intubation device 100. The endotracheal tube 105 includes a proximal end 130 and a distal end 135. The endotracheal tube includes an air injection tube 115 and an inflatable cuff 110. The device further includes a suction trocar 125 which fits within a lighted sleeve 120. The suction trocar may be connected to a suction source (not shown). A preferred light source for the trocar sleeve is fiberoptic. Another preferred light source for the trocar sleeve is chemiluminescent or LEDs. The suction trocar 125 may be made of a malleable material. A preferred malleable material for the suction trocar is aluminum, although polymeric materials such as polyethylene or polypropylene may also be used.

Figure 3:
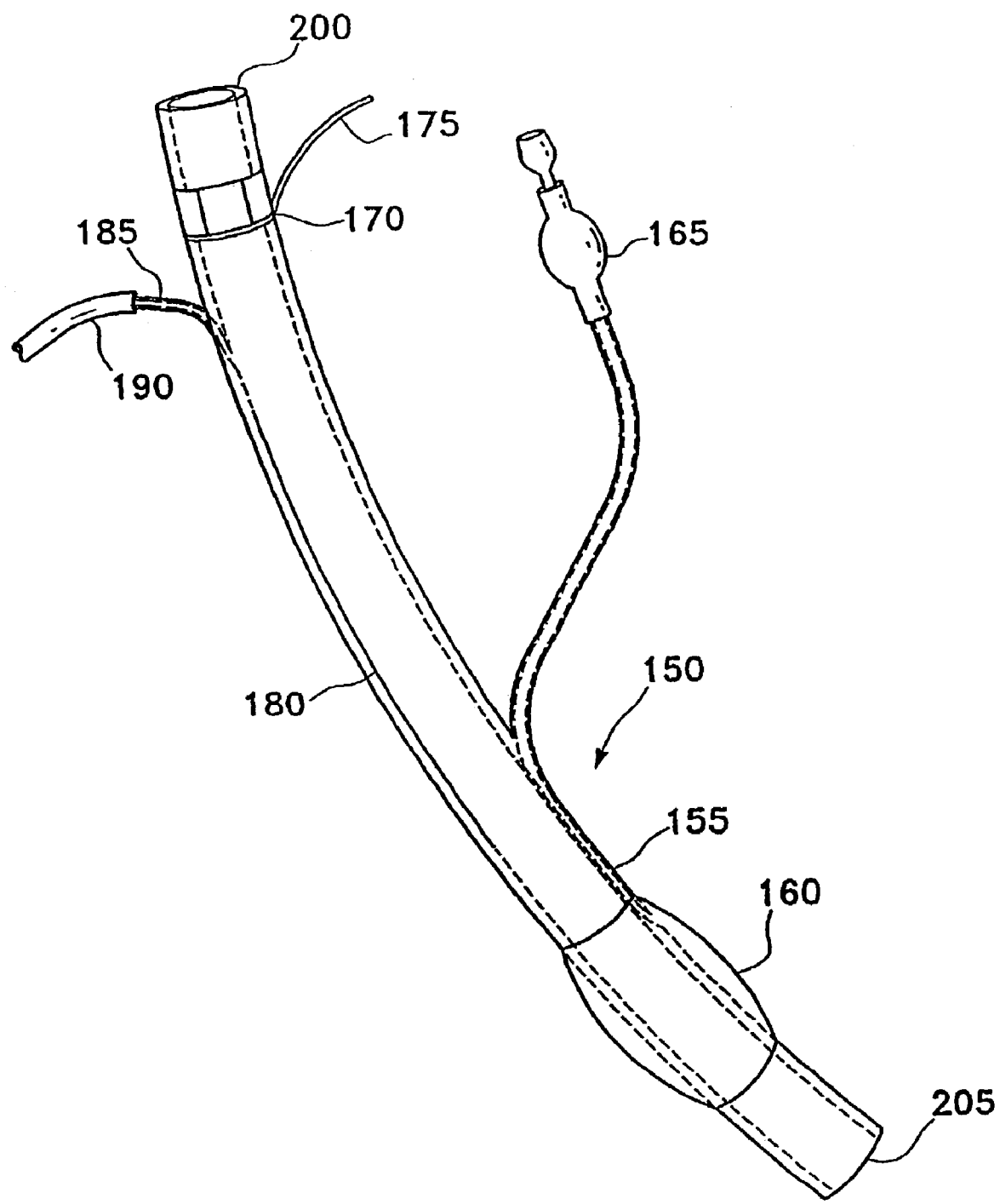
FIG. 3 is a perspective view of an endotracheal intubation device having a light source built into the endotracheal tube and a separate connection to a suction source.

In FIG. 3 is shown another variation of an endotracheal intubation device 150. It includes an endotracheal tube 155 having a proximal end 200 and a distal end 205. The endotracheal tube includes an air injection tube 165 and an inflatable cuff 160. The invention further includes a light source 170 built into the endotracheal tube and a means for connecting the tube to a suction source 185. Flexible tubing 190 may be used to connect the endotracheal tube to a suction motor (not shown). The light source is disposed to shine axially or radially from the proximal end 200 to the distal end 205 of the endotracheal tube. A shape for the light source is a ring of light emitting material. A light source is fiberoptic. A fiberoptic power cord 175 may be used to connect the tube to a fiberoptic power source (not shown). Another light source is chemiluminescent or an LED. The invention may further include a malleable wire 180 for adjusting the shape of the endotracheal tube.

The light emanating from the chemiluminescent light source may be carried from that source by optical fibers or fiberoptics implanted in the wall of the endotracheal tube and extend towards the distal end of the tube. The termination of the optical fibers may be adapted to shine light distally of the endotracheal tube.

Figure 4:
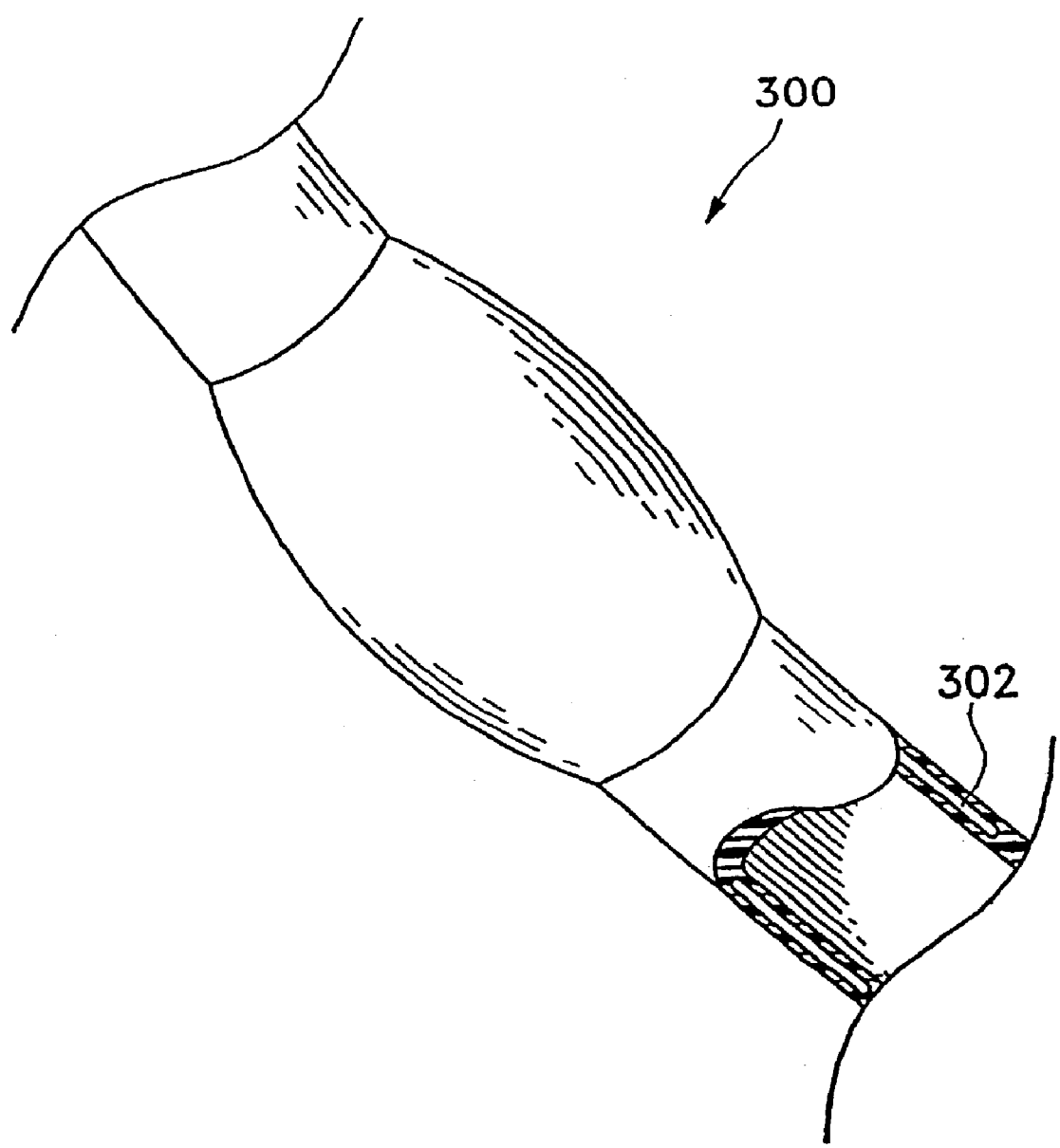
FIG. 4 is a perspective view of an endotracheal intubation device having a chamber for inclusion of a chemiluminescent liquid, gel, or solid.

FIG. 4 shows another variation 300 of the invention. This variation includes a chamber 302 for inclusion of a chemiluminescent liquid, gel, or solid. A preferred variation is the inclusion of an induced or catalyzed chemiluminescent material such as that sold in Cyalume® "Lightstick." Examples of chemiluminescent medical products are described in international patent application PCT/US03/06868, entitled "Chemiluminescently Illuminated Medical Appliances" filed Mar. 6, 2003, incorporated by reference herein in its entirety.

Figure 5:
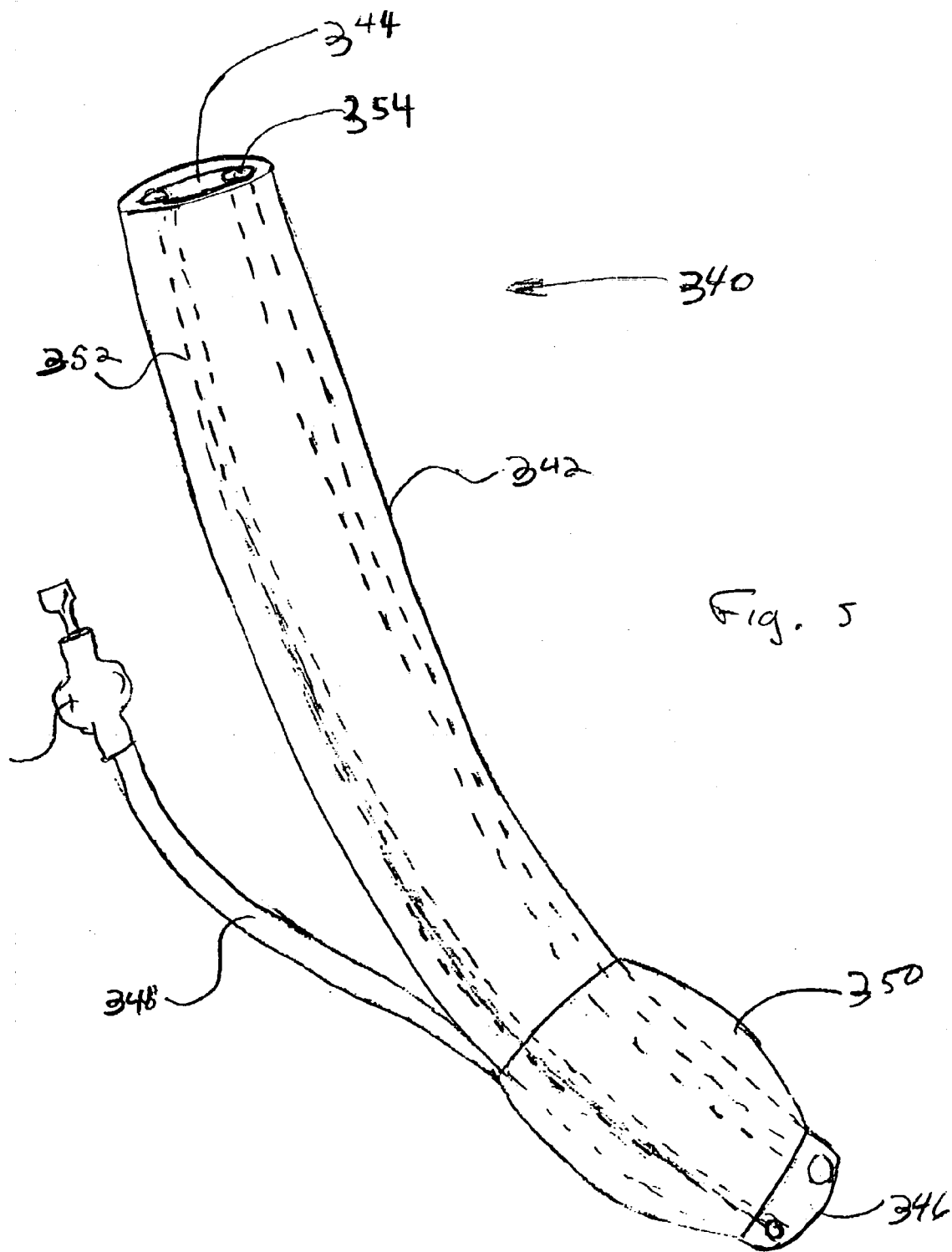
FIG. 5 is a side view of an endotracheal intubation device having longitudinal illumination.

FIG. 5 shows an endotracheal airway intubation device 340 having an endotracheal tube 342 having a proximal end 344 and a distal end 346. The endotracheal tube includes an air injection tube 348 and an inflatable cuff 350. The intubation device may further include a longitudinally situated light source 352 built into the endotracheal tube. Flexible tubing 354 may be used to connect the endotracheal tube to a suction source (not shown). Depending upon the material of construction of the device, this variation can provide chemiluminescent light axially from the ends of the device and/or through the wall of the device. A LED or chemiluminescent capsule may be, for example, a.) connected with the tube, b.) inserted within tube, or c.) attached elsewhere along the device.

The device may further include a malleable wire for adjusting the shape of the endotracheal tube.

It is important to secure the ETT to the face of the patient to prevent it from being moved out of proper position. Tape is not always sufficient. An ETT holder may be desirable that is configured to fit over the mouth and nose of a patient. An adjustable strap may be provided to affix the holder to the patient's face. The holder is adapted to sit over the mouth of the patient and includes an opening that receives the ETT tube. In one variation, the opening includes a laterally-disposed screw that may be tightened, urging the ETT against a support surface. The screw may have an atraumtic tip or adapter so as not to crimp or puncture the ETT tube. Also, the holder may include a battery and switch for activating a LED if the ETT tube is not designed to self illuminate.

FIG. 6 shows a stylet assembly 360 as might be used in intubating a patient needing a temporary airway. Here, the stylet 362 includes a chemiluminescent light source 364 that is coextensive with the stylet shaft 362. Also shown is a handle 366 and an openable ring 368 as might be used with an intubation airway. However, the stylets need not have a handle and ring.

A lighted stylet may also feature a light source positioned at the distal end. The light source may be an LED. Also, the light source may be positioned at the distal end and the stylet may include optical fibers that extend the light to the distal end. The light may be directed to emanate radially and/or axially from the distal end (or another location) of the stylet.

FIG. 7 shows a laryngoscope 370 comprising a laryngeal blade 372 and handle 374. The blade may be curved or straight. The blade may be made of various materials. In one variation, the entire assembly is made of a plastic (e.g., Cycolac manufactured by GE) and the blade includes chemiluminescent or LED components. The blade may be soft such that bending the blade activates chemiluminescent material. Also, the blade's cross section may be curved to facilitate the insertion of other instruments into the throat, providing access to the larynx. Again, the blade 372 may form the outer surface of the chemiluminescent light source. In this way, the throat is illuminated in such a way that an intubation airway may be readily inserted because of the illumination in the patient's throat.

Modifications of the devices described above that are apparent to one of ordinary skill in the art are intended to be within the scope of the claims that follow. Aspects of one device may be combined with that of another described device except where the features are mutually exclusive.

I claim:

1. An illuminated airway product comprising:
   an endotracheal tube having a proximal end, a distal end, and a plurality of lumens extending from the proximal end to the distal end;
   at least an LED mounted in one of said plurality of lumens adjacent the distal end; and
   a voltage source affixed to the endotracheal tube, said voltage source being electrically coupled to said at least an LED.

2. The illuminated airway product of claim 1 further comprising an inflatable cuff, said inflatable cuff being fluidly coupled to one of said plurality of lumens.

3. The illuminated airway product of claim 1 comprising a suction lumen.

4. The illuminated airway product of claim 3 further comprising a suction source fluidly coupled to said suction lumen.

5. The illuminated airway product of claim 1 further comprising a malleable stylet.

6. The illuminated airway product of claim 1 wherein one of said plurality of lumens is a medicinal supply lumen for delivering a medicinal substance.

7. The illuminated airway product of claim 1 wherein the voltage source is a battery.

8. The illuminated airway product of claim 7 wherein said battery has a thickness less than 1 mm.

9. The illuminated airway product of claim 1 further comprising a connector positioned at the proximal end of the endotracheal tube, said connector configured to fluidly couple an airway lumen with an oxygen supply apparatus.

10. The illuminated airway product of claim 1 further comprising a radio-opaque material extending from the proximal end to the distal end through one of said plurality of lumens.

11. The illuminated airway product of claim 1 further comprising a switch secured to said endotracheal tube, said switch configured to activate said at least an LED.

12. The illuminated airway product of claim 11 wherein said switch is resiliently biased in an OFF state and wherein when said switch is pressed, said switch turns to an ON state electrically activating said at least an LED.

13. The illuminated airway product of claim 1 wherein said at least an LED is positioned to direct light at least axially from the endotracheal tube at a tissue to be visualized.

14. The illuminated airway product of claim 1 wherein the voltage source is incorporated proximally into the endotracheal tube.

15. The illuminated airway product of claim 1 wherein said at least an LED is configured to provide visualization during insertion of the distal end of the endotracheal tube into a patient's trachea.

* * * * *